United States Patent [19]

Bobsein

[11] Patent Number: 4,615,836
[45] Date of Patent: Oct. 7, 1986

[54] PROCESS FOR PREPARING ALKYLMERCAPTOALKYL ESTERS

[75] Inventor: Rex L. Bobsein, Bartlesville, Okla.

[73] Assignee: Phillips Petroleum Company, Bartlesville, Okla.

[21] Appl. No.: 611,655

[22] Filed: May 18, 1984

[51] Int. Cl.$^4$ .............................................. C08H 3/00
[52] U.S. Cl. ............................ 260/399; 260/410.9 R; 560/99; 560/222; 560/231
[58] Field of Search ................ 260/410.9 R, 399; 560/99, 222, 231

[56] References Cited

U.S. PATENT DOCUMENTS

| | | | |
|---|---|---|---|
| 2,727,881 | 12/1955 | Caldwell et al. | 260/75 |
| 2,822,348 | 2/1958 | Haslam | 260/75 |
| 3,056,818 | 10/1962 | Werber | 560/99 |
| 3,106,570 | 10/1963 | Jaruzelski et al. | 260/410.5 |
| 3,109,021 | 10/1963 | Elk | 260/486 |
| 3,332,983 | 7/1967 | Barie et al. | 560/179 |
| 3,346,611 | 10/1967 | Doss | 260/455 |
| 3,418,359 | 12/1968 | Barie et al. | 560/179 |
| 3,498,800 | 3/1970 | Warner | 106/14 |
| 3,527,765 | 9/1970 | Reece et al. | 260/327 |
| 3,989,741 | 11/1976 | Parker | 260/486 R |
| 4,007,218 | 2/1977 | Ghanayem et al. | 560/99 |

FOREIGN PATENT DOCUMENTS 17614 8/1982 European Pat. Off. .............. 562/99

OTHER PUBLICATIONS

Chem. Abstracts 85:1923116; V. N. Sapunov et al., "Catalytic Activity of Titanium Catalysts During Esterification".

DuPont brochure on "Polyfunctional Tyzor Organic Titanates", pp. 1–12 and 27.

Primary Examiner—James H. Reamer
Attorney, Agent, or Firm—Edward L. Bowman

[57] ABSTRACT

A process for preparing an alkylmercapto ester by reacting an alkyl mercaptoalkanol with an organic carboxylic acid or an organic anhydride in the presence of a titanium-containing catalyst.

10 Claims, No Drawings

PROCESS FOR PREPARING ALKYLMERCAPTOALKYL ESTERS

The present invention relates to a process for preparing alkyl-mercapto esters directly from an alkyl mercaptoalkanol and an organic carboxylic acid or an organic anhydride.

The term alkylmercapto ester as used herein is intended to include compounds of the formula $$R + C - O - R' - SH)_n$$
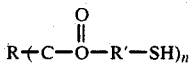

wherein R is an alkyl, cycloalkyl, aryl, alkaryl, or aralkyl group, R' is an alkylene group, and n is at least 1.

It has previously been proposed to prepare such alkylmercapto esters by a direct esterification reaction of a suitable acid and a mercapto alcohol in the presence of an acidic catalyst, such as p-toluenesulfonic acid. It has been found, however, that the rate of ester formation is not as great as is observed when a sulfur free alkanol is used to make an ester. Also it has been noted that the process often results in the formation of solid by-products which are undesirable in many applications of the alkylmercapto esters. Thus in many cases the economics for making the compounds are adversely affected by the low conversion and the necessity for additional purification steps.

SUMMARY OF THE INVENTION

In accordance with the present invention there is provided a method for preparing an alkylmercapto ester comprising reacting an alkylmercapto alkanol with an organic carboxylic acid, or an organic anhydride in the presence of a catalyst comprising a titanium compound in which a titanium atom is bonded through an oxygen atom to a carbon atom free of any double bond with oxygen.

DETAILED DESCRIPTION

The term alkyl mercapto alkanol is used herein to refer to compounds of the formula HO-R'-SH

wherein R' is an alkylene group. Typically the alkylene group would have 2 to 30, more preferably 2 to 15 carbon atoms, and most preferably 2 to 8 carbon atoms. Some typical examples of such compounds include beta-mercaptoethanol, beta-dodecylmercaptoethanol and beta-isooctylmercaptoethanol, beta-heptylmercaptoethanol, 12-dodecylmercaptododecanol, gamma-docosylmercaptopropanol, beta-octasylmercaptoethanol, beta-ethyl mercaptoethanol, 3-mercaptopropanol, beta-methyl mercaptoethanol, 5-mercaptopentanol, and 4-mercaptobutanol.

The term organic carboxylic acid is used herein intended to include compounds having at least one $$-C-OH$$

group bonded to the carbon of an organic radical. Typically the acid will contain 2 to 35 carbon atoms per molecule. Some specific examples include 2-ethylhexanoic acid, acetic acid, butyric acid, acrylic acid, capryl acid, perlargonic acid, lauric acid, myristic acid, palmitic acid, eicosanoic acid, oleic acid, elaidic acid, linoleic acid, linolinic acid, dibenzofurancarboxylic acid, 2-carboxy furan, 2-carboxythiophene, nicotinic acid, cyclohexane carboxylic acid, benzoic acid, napthalene carboxylic acid, anthracene carboxylic acid, phenylacetic acid, stearic acid, isosebacic acid, adipic acid, lacceroic acid, and other acids of the type listed in U.S. Pat. No. 3,106,570 the disclosure of which is incorporated herein by reference. One particularly important acidic reactant is a tall oil fatty acid such as the tall oil fatty acid sold by Union Camp under the tradename Unitol ACD Special.

As noted above it is also within the scope of the present invention to use anhydrides of such organic carboxylic acids. Typical examples include acetic anhydride, maleic anhydride, phthalic anhydride, glutaric anhydride, and succinic anhydride.

Typical titanium compounds within the scope of the above defined catalyst include the ortho esters of the formula Ti(OR")$_4$ wherein R" is an organic radical, particularly an aliphatic hydrocarbon radical. The R" groups can be the same or different. In the currently preferred embodiments each R" group of the ortho ester contains 3 to 8 carbon atoms. The condensed esters or polytitanic acid esters are also within the scope of the broad definition of the catalyst. Such can be produced by reacting an ortho ester with less than an equivalent quantity of water. Still another general type of titanium compound are the titanium ester carboxylates or titanium ester acylates formed by reacting a titanium ortho ester with a fatty acid. Some specific examples of titanium compounds falling within the scope of the above definition are tetraisopropyl titanate, tetra-n-butyl titanate, tetrakis (2-ethylhexyl) titanate, titanium acetyl acetonate, the triethanolamine titanium chelate containing two isopropyl oxy groups, lactic acid titanium chelate containing two isopropyl oxy groups, and titanium ethyl acetoacetate chelate containing two isopropyl oxy groups. Forms of the last four titanium compounds have been sold by Du Pont under the tradenames Tyzor AA, Tyzor TE, Tyzor LA, and Tyzor DC, respectively.

The alkylmercapto alkanol and the acid or anhydride can be reacted in any suitable proportions. It is sometimes advantageous to use an excess of one of the two to help drive the reaction to the desired product. In that same vein it is desirable to remove water from the reaction zone as it forms. This can be accomplished by carrying the reaction out under reflux and contacting the vapors with a material which will absorb the water. The temperature employed can vary over a wide range depending upon the reactants selected and the desired rate of conversion. Typically however the temperature will be in the range of about 30° C. to about 200° C., more preferably about 90° C. to about 160° C. It is generally desirable to carry out the reaction in the presence of a liquid diluent that does not adversely affect the reaction. Toluene and xylene are typical examples of liquids which have been found suitable as diluents. The time required will depend to some degree upon the reactants, the catalyst, the proportions of reactants and catalyst, and the temperature.

The amount of the titanium catalyst employed can vary substantially. Normally, it would be used in the smallest amount compatible with a reasonable reaction rate. Generally, however, an amount would be used that would be equal to about 0.01 to about 10 weight percent, more preferably about 0.05 to about 5 weight percent, of the weight of the stoichiometric amount of the acid. As used herein the term stoichiometric is intended to refer to the amount of the acid employed that could theoretically react with the amount of the alcohol employed. Thus if an excess of acid is employed, the stoichiometric amount of the acid will be less than the total amount of the acid employed.

The alkylmercapto esters of the type described herein have numerous known uses. Many are suitable for use in tarnish preventive compositions as disclosed in U.S. Pat. No. 3,498,800. Many are also suitable as additives for various polymer compositions. The alkyl mercaptoalkyl esters of unsaturated monocaboxylic acids are useful as intermediates for the production of polymers which are useful as additives in hydrocarbon fuels and oils as disclosed in U.S. Pat. No. 3,109,021.

A further understanding of the present invention and its advantages over the prior art will be provided by the following examples.

EXAMPLE 1

Beta-mercaptoethanol (171.1 grams, 2.2 moles), 2-ethylhexanoic acid (156.2 grams, 1.1 moles), and 3.0 mL of tetrabutyl titanate were placed in 600 mL of xylene in a 3-necked round bottom flask fitted with a magnetic stirrer, a Dean-Stark trap, a reflux condenser and heated with a mantle. The mixture was stirred and refluxed at atmospheric pressure for 31.5 hours. An azeotrope of xylene, water and mercaptoethanol is formed in the vapor state and most of the water separates in a layer in the trap. The progress of the reaction was monitored by g.l.c. analysis and by the formation of water. Reaction was continued until the rate of water formation had decreased considerably and the g.l.c. indicated very little 2-ethyl hexanoic acid remained. The solvent was removed in a rotary evaporator and the product mixture analyzed by g.l.c. which showed a conversion of 89.6% of the 2-ethylhexanoic to 2-mercaptoethyl 2-ethylhexanoate. The product ester had a slight color. A clear, water-white product was obtained by distillation. IR analysis showed a loss of acid bands at 3030 cm$^{-1}$ $(-OH)$ and

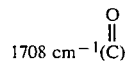

and new ester band at 1733 cm$^{-1}$. Also mercaptan sulfur of 13.3% proves it is an O-ester, not an S-ester.

EXAMPLE 2

Using procedures and apparatus as in Example 1 but with variations in reactants, catalyst and reaction time as noted, the following additional runs demonstrate the improvement realized by the use of the tetrabutyl titanate catalyst in the esterification of 2-mercaptoalcohols as compared with other catalysts.

TABLE I

| | | Formation of 2-Mercaptoethyl 2-Ethylhexanoate by Esterification of 2-Mercaptoethanol | | | | | | |
|---|---|---|---|---|---|---|---|---|
| Run | 2-Mercapto-ethanol (moles) | 2-Ethyl-hexanoic Acid (moles) | Solvent | Catalyst Type* | Amount | Reaction Time, Hrs | Solids Formed | Acid Conv., % (by GLC) |
| 1 | 0.055 | 0.055 | Xylene | H$_2$SO$_4$ | 2 drops | 1.00 | Yes | 3.7 |
| 2 | 0.029 | 0.029 | Toluene | TSA | 0.04 gm | 10.25 | Yes | 12.8 |
| 3 | 0.056 | 0.056 | Toluene | BTA | 0.5 ml | 9.25 | No | 2.1 |
| 4 | 0.053 | 0.053 | Xylene | Amb. 15 | 1.87 g | 5.0 | Yes | 2.5 |
| 5 | 0.040 | 0.040 | Xylene | TBT | 0.5 ml | 15.0 | Trace | 36.4 |
| 6 | 0.064 | 0.032 | Xylene | TBT | 0.5 ml | 17.25 | No | 79.0 |
| 7 | 2.190 | 1.083 Tall oil Fatty Acid | Xylene | TBT | 3.0 ml | 31.5 | No | 89.6 |
| 8 | 2.047 | 1.015 | Xylene | TBT | 2.0 | 15.0 | No | ~100 |
| 9 | 2.042 | 1.009 | Xylene | TBT | 2.0 | 14.0 | No | ~100 |

*TSA = p-Toluene Sulfonic Acid
BTA = Dibutyl Tin Diacetate
Amb 15 = Amberlyst 15
TBT = Tetrabutyl Titanate It is seen that by-products, which are usually solids, are formed in the presence of some of the catalysts. The use of tetrabutyl titanate minimizes or avoids this problem.

EXAMPLE 3

The following examples further demonstrate the advantages of the use of TBT. The procedure was the same as in Example 1 but the equipment was on a smaller scale. The reaction conditions were the same in each case except for the use of the different catalysts as noted.

TABLE II

| | | Esterification of 2-Mercaptoethanol with 2-Ethylhexanoate | | | | | | |
|---|---|---|---|---|---|---|---|---|
| Run | 2-Mercapto-ethanol (moles) | 2-Ethyl hexanoic Acid (moles) | Solvent Type | mL | Catalyst Type* | Amount | Reaction Time, Hrs | Acid Conv., % (by GLC) |
| 10 | 0.056 | 0.029 | xylene | 100 | H$_2$SO$_4$ | 0.5 mL | 20 | trace |
| 11 | 0.056 | 0.029 | xylene | 100 | TBT | 0.5 mL | 20 | 87.6 |
| 12 | 0.056 | 0.029 | xylene | 100 | pTSA | 0.5 gm | 20 | trace |

TBT = Tetrabutyl Titanate
pTSA = p-Toluene Sulfonic Acid

Under otherwise identical conditions it is seen that in the esterification of 2-mercaptoethanol, TBT is greatly superior to the other catalysts tested. The titanium catalyst results in a product substantially free of solids. It also clearly results in a much greater rate of conversion, a point that is not suggested by the results obtained when the catalyst is used in an esterification involving a sulfur-free alkanol.

What is claimed is:

1. A process for preparing an alkylmercapto ester free of substantial amounts of solid by-products comprising reacting beta-mercaptoethanol with an organic carboxylic acid containing 2 to 35 carbon atoms per molecule or anhydrides of such carboxylic acids in the presence of a catalyst comprising a titanium compound of the formula Ti(OR″)$_4$ wherein R″ is an organic radical having 3 to 8 carbon atoms.

2. A process according to claim 1 wherein an alkylmercapto alkanol is reacted with an organic carboxylic acid.

3. A process according to claim 2 wherein said organic carboxylic acid comprises tall oil fatty acid.

4. A process according to claim 3 wherein said catalyst comprises tetra-n-butyl titanate.

5. A process according to claim 2 wherein said catalyst comprises tetra-n-butyl titanate.

6. A process according to claim 5 wherein said organic carboxylic acid consists essentially of 2-ethyl hexanoic acid.

7. A process according to claim 2 wherein said carboxylic acid has the formula

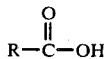

wherein R is an alkyl, cycloalkyl, aryl, alkaryl, or aralkyl group containing 1 to 34 carbon atoms.

8. A process according to claim 7 wherein said catalyst comprises tetra-n-butyl titanate.

9. A process for preparing an alkylmercapto ester comprising reacting 2-ethyl hexanoic acid with beta-mercapto-ethanol in the presence of a catalyst comprising tetra-n-butyl titanate.

10. A process for preparing an alkylmercapto ester comprising reacting tall oil fatty acid with beta-mercapto-ethanol in the presence of a catalyst comprising tetra-n-butyl titanate.

* * * * *